(12) United States Patent
Sitharaman et al.

(10) Patent No.: US 9,833,522 B2
(45) Date of Patent: Dec. 5, 2017

(54) GRAPHENE-BASED CONTRAST AGENTS FOR PHOTOACOUSTIC AND THERMOACOUSTIC TOMOGRAPHY AND METHOD OF USE

(71) Applicant: THE RESEARCH FOUNDATION FOR THE STATE UNIVERSITY OF NEW YORK, Albany, NY (US)

(72) Inventors: Balaji Sitharaman, Coram, NY (US); Gaurav Lalwani, Indore (IN)

(73) Assignee: The Research Foundation for The State University of New York, Albany, NY (US)

(*) Notice: Subject to any disclaimer, the term of this patent is extended or adjusted under 35 U.S.C. 154(b) by 26 days.

(21) Appl. No.: 14/581,690

(22) Filed: Dec. 23, 2014

(65) Prior Publication Data
US 2015/0182642 A1    Jul. 2, 2015

Related U.S. Application Data

(60) Provisional application No. 61/920,282, filed on Dec. 23, 2013.

(51) Int. Cl.
*A61K 49/22*    (2006.01)
*A61K 49/00*    (2006.01)

(52) U.S. Cl.
CPC ............ *A61K 49/222* (2013.01); *A61K 49/00* (2013.01)

(58) Field of Classification Search
CPC ................................ A61K 49/00; A61K 49/22
See application file for complete search history.

(56) References Cited

U.S. PATENT DOCUMENTS

2007/0299341 A1* 12/2007 Wang ................... A61B 5/0091
600/443

FOREIGN PATENT DOCUMENTS

WO    WO 2012/154677    * 11/2012

OTHER PUBLICATIONS

Matthew C. Duch et al. Minimizing Oxidation and Stable Nanoscale dispersion improves the Biocompatibility of Graphene in the Lung, Nano Letter, 2011, 11, 5201-5207.*
Zhuang Liu et al., Nano-graphene in biomedicine: theranostic applications, Chem Soc Rev 2013, 42, 530-547.*
Yin Zhang et al., Graphene: a versatile nanoplatform for biomedical applications, Nanscale, 2012, 4, 3833-3842.*

* cited by examiner

*Primary Examiner* — Michael G Hartley
*Assistant Examiner* — Jagadishwar Samala
(74) *Attorney, Agent, or Firm* — Scully, Scott, Murphy & Presser, P.C.

(57) ABSTRACT

The present invention provides a composition for use with photoacoustic or thermoacoustic imaging, comprising a sufficient amount of the graphene-like nanoparticles or graphitic nano- or microparticles and one or more physiologically acceptable carriers or excipients. The present invention also provides methods of using the graphene-like nanoparticles or graphitic nano- or microparticles as PAT/TAT contrast agents.

29 Claims, 6 Drawing Sheets

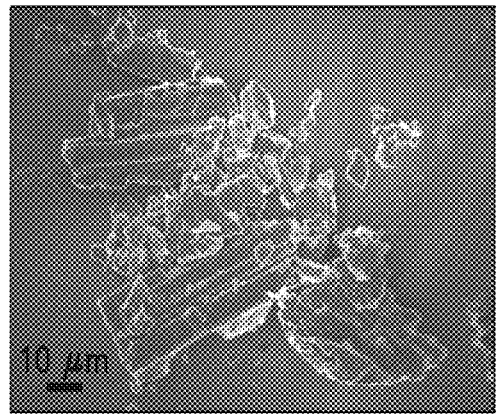 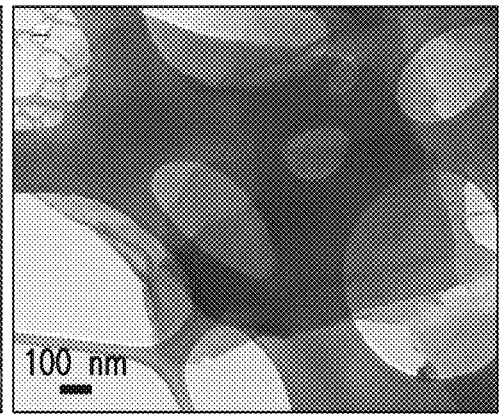
FIG. 1E  FIG. 1F
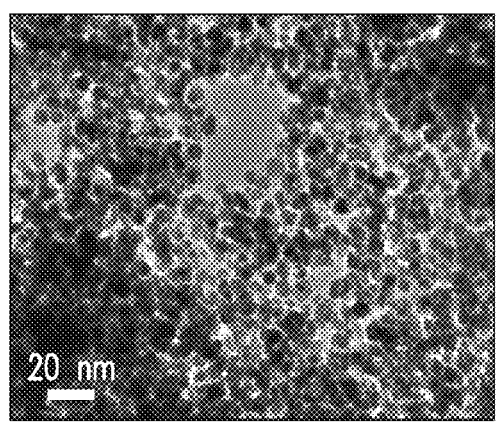
FIG. 1G

GRAPHENE-BASED CONTRAST AGENTS FOR PHOTOACOUSTIC AND THERMOACOUSTIC TOMOGRAPHY AND METHOD OF USE

REFERENCE TO RELATED APPLICATIONS

This application claims priority to U.S. Provisional Application No. 61/920,282, filed Dec. 23, 2013, the content of which is incorporated herein by reference in its entirety.

FEDERAL FUNDING

This invention was made with government support under grant number OD007394 awarded the National Institutes of Health. The federal government has certain rights in the invention.

FIELD OF THE INVENTION

The present invention relates to graphene-like nanoparticles and graphitic nano- or microparticles and method for production thereof. The present invention also relates to methods of graphene-like nanoparticles or graphitic nano- or microparticles as contrast agents for photoacoustic and/or thermoacoustic tomography.

BACKGROUND OF THE INVENTION

Photoacoustic (PA) tomography [1] and thermoacoustic (TA) tomography [2] (hereafter referred as PAT/TAT) have been developed as hybrid biomedical imaging modalities suitable for applications in bioimaging. PAT/TAT combines the advantages of pure ultrasound and pure optical/radio frequency (rf) imaging, providing good spatial resolution, great penetration depth, and high soft-tissue contrast. These imaging modalities are based on the detection of acoustic waves from an object that absorbs electromagnetic energy (for example, a PAT system uses laser whereas a TAT system uses a microwave excitation source). Recently, high resolution PAT and/or TAT have been used for advanced imaging applications such as functional brain imaging [3,4], early breast cancer detection [5,6], melanoma detection [7,8], tumor angiogenesis [9,10] and functional molecular imaging [11].

The development of PAT and TAT as hybrid biomedical imaging modalities has led concurrently to increased use of chemical contrast-enhancement products called contrast agents (CAs) which improve detection of pathologic lesions by increasing sensitivity and diagnostic confidence. For example, it is known that optical absorption in biological tissues is due to or induced by endogenous molecules such as hemoglobin, melanin, and water/ion. However, in the cases when endogenous molecules are insufficient, exogenous contrast agents would have to be administered. Contrast-enhanced PAT imaging can be used for non-invasive characterization of levels of vascularization and oxygen saturation of tissues and serves as tool to monitor tissue regeneration. In particular, contrast-enhanced PAT has been applied in lymph node mapping [12], multiscale imaging of tissue engineering scaffolds [13-15], and molecular, cellular, and functional imaging [16-19]. A variety of contrast agents for PAT have been reported, such as, carbon nanoparticles [12, 20-22], metallic nanoparticles [17-19, 23-25], and organic dyes [26]. In comparison to PAT, fewer reports have focused on development of contrast agents for TAT in biomedical applications. Among them, superparamagnetic iron oxide nanoparticles, and single- and multi-walled carbon nanotubes (SWCNT and MWCNT) have been investigated as TA contrast agents [2, 21].

Most recently, oxidized graphene nanoplatelets (O-GNPs) and oxidized graphene nanoribbons (O-GNRs) have also been reported as contrast agents for other whole-body imaging applications such as magnetic resonance imaging [28] and nuclear imaging [32]. The results of these and other reports suggest the possibility of their development as multimodal contrast agents that provide complementary information at micro- to macro-scopic length scales. Furthermore, these graphene nanoparticles can be functionalized for targeted therapeutics, drug delivery and cellular/molecular imaging applications [33], and thus, show potential as multifunctional nanoparticles. Indeed, several in vitro and in vivo safety and efficacy studies on these graphene nanoparticles have been reported for various biomedical applications [29,33,41].

SUMMARY OF THE INVENTION

The present invention provides a composition for use with photoacoustic or thermoacoustic imaging, comprising a sufficient amount of a graphene-like nanostructure or a graphitic nano- or microstructure; and one or more physiologically acceptable carriers or excipients.

The graphene-like nanostructure can be a carbon nanoplatelet or a carbon nanoribbon. The carbon nanoplatelet or carbon nanoribbon can be oxidized. Preferably, the graphene-like nanostructure, e.g., the carbon nanoplatelet or the carbon nanoribbon, has a thickness of about 50 nm or less, 45 nm or less, 30 nm or less, 25 nm or less, 20 nm or less, 15 nm or less, 10 nm or less, 5 nm or less, at least 3 to 4 atomic carbon sheets, at least 5 atomic carbon sheets, or at least 10 atomic carbon sheets.

Preferably, the graphitic nanostructure or microstructure has a thickness of 5 μm or less, 4 μm or less, 3 μm or less, 2 μm or less, 1 μm or less, 500 nm or less, 250 nm or less of 100 nm or less.

Preferably, the carbon nanoplatelet having an average diameter in the range of 5 to 100 nm, 10 to 75 nm, 20 to 50 nm, or 30 to 40 nm. Preferably, the carbon nanoribbon having an average width in the range of 1 to 250 nm, 10 to 200 nm, 50 to 150 nm, or 70 to 100 nm.

The graphitic nanostructure or microstructure may further comprise one or more magnetic metals and can be paramagnetic, diamagnetic, or ferromagnetic. The magnetic composition can also be superparamagnetic. In one embodiment, the magnetic metal is a room temperature paramagnetic metallic element, including but not limited to inner-transition metal Mn. In another embodiment, the magnetic metal is a room temperature ferromagnetic metallic element including but not limited to inner-transition metals Fe, Co, and Ni. In still another embodiment, the magnetic metal is a rare earth metal, including but not limited to lanthanoids Gd, Eu, Pr, Nd, and Sm. Preferred magnetic metals that can be used in the present invention include Mn, Gd, and Fe.

The magnetic metal can be present in the magnetic composition as an ion. The magnetic metal can also be present in the magnetic composition in the form of a metal compound, including but not limited to a metal oxide and a metal salt. The magnetic metal or compound thereof can be intercalated in the graphene-like nanostructure or graphitic nano- or microstructure.

The magnetic composition of the present invention can comprise the magnetic metal in an amount in the range of 1 ppb (mass parts per billion) to $10^7$ ppm (mass parts per million), $10^2$ ppb to $10^6$ ppm, 1 ppm to $10^5$ ppm, 10 to $10^4$ ppm, or $10^2$ to $10^3$ ppm.

The graphene-like nanostructure or graphitic nano- or microstructure can further comprise a water solubilizing moiety attached to the graphene-like nanostructure or microstructure, e.g., covalently attached to the graphene-like nanostructure or graphitic nano- or microstructure. The graphene-like nanostructure or graphitic nano- or microstructure can further be dispersed in water using 1,2-distearoyl-sn-glycero-3-phosphoethanolamine-N-amino(polyethylene glycol) (DSPE-PEG) or Pluronic® for improving water solubility.

The present invention also provides a method of performing photoacoustic or thermoacoustic imaging of a subject, comprising administering to the subject a sufficient amount of the composition of the invention; and imaging the subject using a photoacoustic or thermoacoustic imaging device. Compositions of the invention are also suitable for theragnostic applications. The subject can be any animal, including but not limited to a mammal, e.g., a human.

BRIEF DESCRIPTION OF THE FIGURES

FIG. 1(A)-1(G). Representative transmission electron microscopy images of (FIG. 1A) single-walled carbon nanotubes (SWCNTs), (FIG. 1) multi-walled carbon nanotubes (MWCNTs), (FIG. 1C) oxidized single-walled graphene nanoribbons (O-SWGNRs), (FIG. 1D) oxidized multi-walled graphene nanoribbons (O-MWGNRs), (FIG. 1F) oxidized graphite microparticles (O-GMP), and (FIG. 1G) exfoliated graphene nanoplatelets (O-GNP). Image (FIG. 1E) is a scanning electron micrograph of pristine GMPs.

DETAILED DESCRIPTION OF THE INVENTION

Figure 1A:
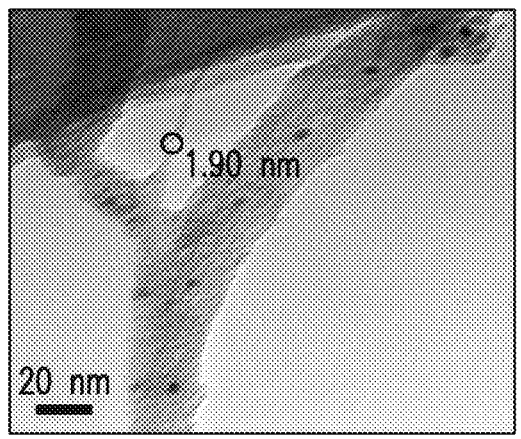
Figure 1B:
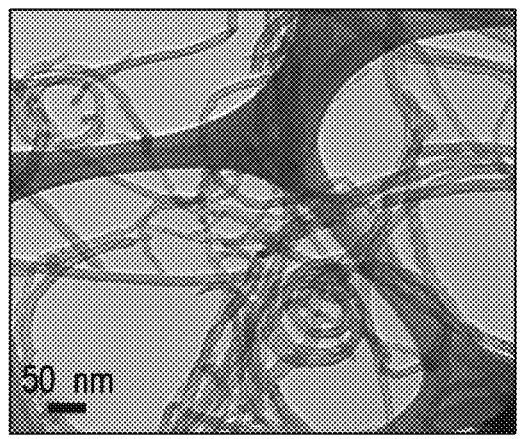
Figure 1C:
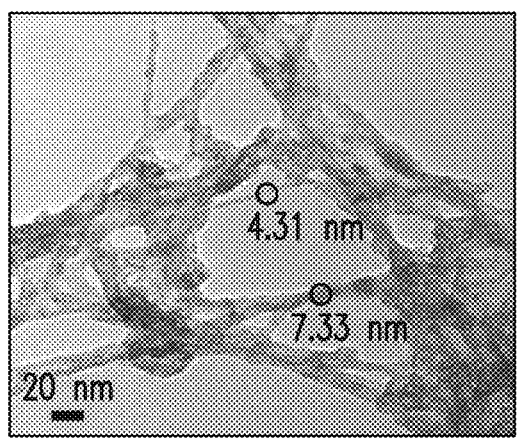
Figure 1D:
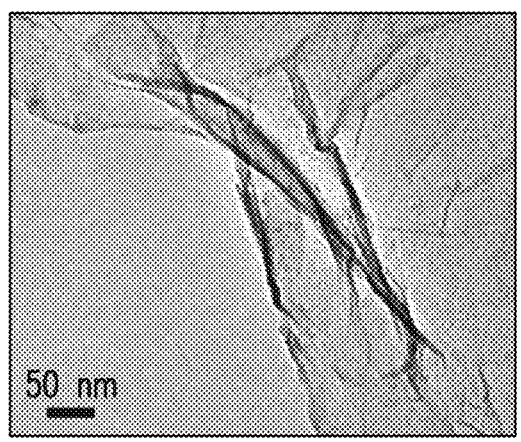

The present invention provides a composition for use with photoacoustic or thermoacoustic imaging, comprising a sufficient amount of a graphene-like nanostructure or a graphitic nano- or microstructure; and one or more physiologically acceptable carriers or excipients. Graphene is a flat monolayer of carbon atoms tightly packed into a two-dimensional (2D) honeycomb lattice, and is a basic building block for graphitic materials of all other dimensionalities, and which can be wrapped up into OD fullerenes, rolled into 1D nanotubes or stacked into 3D graphite (Geim and Novoselov, 2007, "The rise of graphene", *Nature Materials* 6 (3): 183-191). As used herein, the term "graphene-like nanostructure" (or "graphene-like nanoparticle") refers to a carbon nanostructure comprising one or more atomic carbon sheets or layers. In the present application, for simplicity reasons, the term "graphene nanostructure" (or graphene nanoparticle") is also used to refer to a graphene-like nanostructure or graphene-like nanoparticle. Thus, unless expressly stated, the term "graphene nanostructure" is not limited to a nanostructure having only a single atomic carbon sheet. The graphene-like nanostructure can be a carbon nanoplatelet or a carbon nanoribbon. The carbon nanoplatelet or carbon nanoribbon can be oxidized.

Preferably, the graphitic nanostructure or microstructure has a thickness of 5 μm or less, 4 μm or less, 3 μm or less, 2 μm or less, 1 μm or less, 500 nm or less, 250 nm or less of 100 nm or less.

In one embodiment, the graphitic microstructure (or graphitic microparticle) has a thickness in the range of 1 to 5 μm, 2 to 4 μm, or 2 to 3 μm. The graphitic microstructure can comprise 5 to 10 atomic carbon sheets. In one embodiment, the graphitic microstructure is 65 μm or less, 55 μm or less, 45 μm or less, 35 μm or less or 25 μm or less in size. In a specific embodiment, the graphitic microstructure has a size of less then 45 μm.

In another specific embodiment, the graphitic microstructure has about 8 atomic carbon sheets.

Preferably, the graphene-like nanostructure, e.g., the carbon nanoplatelet or the carbon nanoribbon, has a thickness of about 20 nm or less, 15 nm or less, 10 nm or less, 5 nm or less or 3 nm or less. The graphene-like nanostructure, e.g., the carbon nanoplatelet or the carbon nanoribbon, can comprise at least 1 atomic carbon sheet, at least 2 atomic carbon sheets, at least 5 atomic carbon sheets, or at least 10 atomic carbon sheets. In one embodiment, the graphene-like nanostructure, e.g., the carbon nanoplatelet or the carbon nanoribbon, comprises 1 to 12 atomic carbon sheets. In a specific embodiment, the graphene-like nanostructure, e.g., the carbon nanoplatelet or the carbon nanoribbon, comprises 2 to 4 atomic carbon sheets.

Preferably, the graphene-like nanostructure is a carbon nanoplatelet having an average diameter in the range of 5 to 100 nm, 10 to 75 nm, 20 to 50 nm, or 30 to 40 nm. In a specific embodiment, the carbon nanoplatelet has a diameter of about 5 to 15 nm. In still another specific embodiment, the graphene-like nanoplatelet has a thickness in the range of 1 to 5 nm and a diameter of about 50 nm.

Preferably, the graphene-like nanostructure is a carbon nanoribbon having an average width in the range of 1 to 250 nm, 10 to 200 nm, 50 to 150 nm, or 70 to 100 nm. In a specific embodiment, the carbon nanoribbon has an average width of about 120 nm. Preferably, the carbon nanoribbon has an average length in the range of 200 to 5000 nm, 400 to 4000 nm, or 500 to 3000 nm. In a specific embodiment, the carbon nanoribbon has an average length in the range of 600 to 2000 nm.

The graphene-like nanostructure or graphitic nano- or microstructure can be magnetic and comprise one or more magnetic metals and a graphene-like nanostructure or graphitic nano- or microstructure. The magnetic composition can be paramagnetic or diamagnetic. Preferably, the magnetic composition is paramagnetic. The magnetic composition can be ferromagnetic. The magnetic composition can also be superparamagnetic.

The magnetic metal in the magnetic composition of the present invention can be any metal that exhibits magnetism in the presence or absence of an externally applied magnetic field. In one embodiment, the magnetic metal is a room temperature paramagnetic metallic element, including but not limited to inner-transition metal Mn. In another embodiment, the magnetic metal is a room temperature ferromagnetic metallic element including but not limited to inner-transition metal Fe, Co, and Ni. In still another embodiment, the magnetic metal is a rare earth metal, including but not limited to lanthanoid Gd, Eu, Pr, Nd, and Sm. Preferred magnetic metals that can be used in the present invention include Mn, Gd, and Fe.

The magnetic composition can comprise more than one magnetic metal. In one embodiment, the magnetic composition comprises two different magnetic metals. In a preferred embodiment, the magnetic composition comprises Mn and Fe.

The magnetic metal can be present in the magnetic composition as an ion. The magnetic metal can also be present in the magnetic composition in the form of a metal compound, including but not limited to a metal oxide and a metal salt. In a preferred embodiment, the magnetic metal is present in the magnetic composition in the form of a metal oxide.

In a preferred embodiment, the magnetic metal or compound thereof is intercalated in the graphene-like nanostructure or graphitic nano- or microstructure.

The magnetic composition of the present invention can comprise the magnetic metal in an amount in the range of 1 ppb (mass parts per billion) to $10^7$ ppm (mass parts per million), $10^2$ ppb to $10^6$ ppm, $10^2$ ppb to $10^2$ ppm, 1 ppm to $10^5$ ppm, 10 to $10^4$ ppm, or $10^2$ to $10^3$ ppm.

A composition comprising a magnetic metal and a graphene-like carbon nanostructure can be made by oxidizing graphite with a mixture of sulfuric acid $H_2SO_4$, nitric acid ($HNO_3$) sodium nitrate $NaNO_3$, manganese chloride ($MnCl_2$), and potassium permanganate $KMnO_4$; and sonicating a suspension of the product obtained. The magnetic composition may be reduced with a reducing agent. In one embodiment, the reducing agent is hydrazine hydrate. In one embodiment, the graphite used in the method of the invention is micro-graphite, e.g., having a size of about 45 µm.

The graphene-like nanostructures can be prepared using any method known in the art, e.g., using longitudinal unzipping method [27] and modified Hummer's method of oxidation [28].

The graphene-like nanostructure or graphitic nano- or microstructure can further comprise a water solubilizing moiety attached to the graphene-like nanostructure or microstructure. In one embodiment, the water solubilizing moiety is covalently attached to the graphene-like nanostructure or graphitic nano- or microstructure. In a specific embodiment, the water solubilizing moiety is selected from the group consisting of malonic acid, serinol malonodiamide, dextran, and a cyclodextrin, attached to the graphene-like nanostructure or graphitic nano- or microstructure. The water solubilizing moiety can be attached to the graphene-like nanostructure or graphitic nano- or microstructure using any method known in the art, e.g., using Bingel type reactions (Bingel, C., 1993, Cyclopropanierung von Fullerenen, Chemische Berichte 126 (8):1957). The graphene-like nanostructure or graphitic nano- or microstructure can further be dispersed in water using DSPE-PEG or Pluronic® for improving water solubility.

The present invention also provides a method of performing photoacoustic or thermoacoustic imaging of a subject, comprising administering to the subject a sufficient amount of the composition of the invention; and imaging the subject using a photoacoustic or thermoacoustic imaging device. The subject can be any animal, including but not limited to a mammal. In a preferred embodiment, the subject is a human. The composition of the invention can be used alone or in combination with another agent, including but not limited to another PAT/TAT contrast agent. The composition can be administrated to the subject by any method known in the art, including but not limited to intravascular injection and oral administration. A person skilled in the art would be able to select the appropriate administration route according to the tissue, organ or other region in the body of interest and/or the purposes of the scan. Photoacoustic or thermoacoustic imaging can be carried by any standard method and device known in the art.

In a preferred embodiment, the present invention provides a method of performing photoacoustic imaging or thermoaccoustic imaging of a subject, comprising administering to the subject a sufficient amount of the carbon nanoribbon of the present invention. In another preferred embodiment, the present invention provides a method of performing thermoacoustic imaging of a subject, comprising administering to the subject a sufficient amount of the carbon nanoplatelet of the present invention. In still another preferred embodiment, the present invention provides a method of performing thermoacoustic imaging of a subject, comprising administering to the subject a sufficient amount of the graphitic microstructures of the present invention.

The compositions for use in accordance with the present invention may be formulated in conventional manner using one or more physiologically acceptable carriers or excipients depending on, e.g., the route for administration, e.g., oral or parenteral administration.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, lipids, or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. In a specific embodiment, the composition of the present invention is dispersed in a 1,2-distearoyl-sn-glycero-3-phosphoethanolamine-N-amino(polyethylene glycol) (DSPE-PEG).

The compounds may be formulated for parenteral administration by injection, e.g., by bolus injection or continuous infusion. Formulations for injection may be presented in unit dosage form, e.g., in ampoules or in multi-dose containers. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Suitable routes of administration may, for example, include oral and parenteral delivery, including intramuscular, subcutaneous, intramedullary injections, as well as intrathecal, direct intraventricular, intravenous, intraperitoneal, intranasal, or intraocular injections.

Furthermore, one may administer the drug in a targeted drug delivery system, for example, in a liposome coated with an antibody specific for affected cells. The liposomes will be targeted to and taken up selectively by the cells of interest.

The compositions may, if desired, be presented in a pack or dispenser device, which may contain one or more unit dosage forms containing the magnetic composition. The pack or dispenser device may be accompanied by instructions for administration. Compositions comprising a magnetic composition of the invention formulated in a compatible carrier may also be prepared, placed in an appropriate container, and labeled for use.

Throughout this application, various publications are referenced. These publications are hereby incorporated into this application by reference in their entireties.

EXAMPLES

The following examples are presented by way of illustration of the present invention, and are not intended to limit the present invention in any way.

Materials and Methods:
Synthesis and Characterization of Nanomaterials:

Single-walled carbon nanotubes (SWCNTs) (purchased from Cheap Tubes Inc., VT, USA) and multi-walled carbon nanotubes (MWCNTs) (purchased from Sigma Aldrich, NY, USA) were used as received. Oxidized single- and multi-walled graphene oxide nanoribbons (O-SWGNRs, O-MWGNRs), and oxidized graphene nanoplatelets (O-GNPs) were synthesized using previously reported procedures [27, 28, 29]. In particular, oxidized single- and multi-walled graphene oxide nanoribbons (O-SWGNRs and O-MWGNRs) were prepared by the longitudinal unzipping method using pristine single- and multi-walled carbon nanotubes (SWCNTs and MWCNTs), respectively, as the starting material. Oxidized graphene nanoplatelets (O-GNPs) were prepared by modified Hummers method using pristine graphitic microparticles (GMPs) (purchased from Sigma Aldrich, NY, USA) as the starting material. Oxidized graphitic microparticles (O-GMPs) are the intermediate product formed during the synthesis of oxidized graphene nanoplatelets (O-GNPs). These nanomaterials were characterized by Raman spectroscopy and electron microscopy. Raman spectroscopic characterization of SWCNTs, MWCNTs, O-SWGNRs, O-MWGNRs, GMPs, O-GMPs, and O-GNPs has been previously reported [28-30, 31]. All the nanomaterials were dispersed at 5 mg/ml in DSPE-PEG for PA and TA signal measurements.

Photoacoustic (PA) Imaging:

A deep reflection-mode PA imaging system was used (Scheme 1 in ref.[35]) for PA tests of the graphene samples. A tunable Ti:sapphire laser (LT-2211A; Lotis TII, Minsk, Belarus) pumped by a Q-switched Nd:YAG (LS-2137; Lotis TII) laser was used for PA excitation (pulse width: 5 ns, pulse repetition rate: 10 Hz). A 5-MHz central frequency, spherically focused ultrasonic transducer (V308; Panametrics-NDT, Waltham, Mass., USA) was used to acquire the generated PA signals. The signal was amplified by a low-noise amplifier (5072PR; Panametrics-NDT), and recorded using a digital oscilloscope (TDS 5054; Tektronix, Beaverton, Oreg., USA).

Figure 3A:
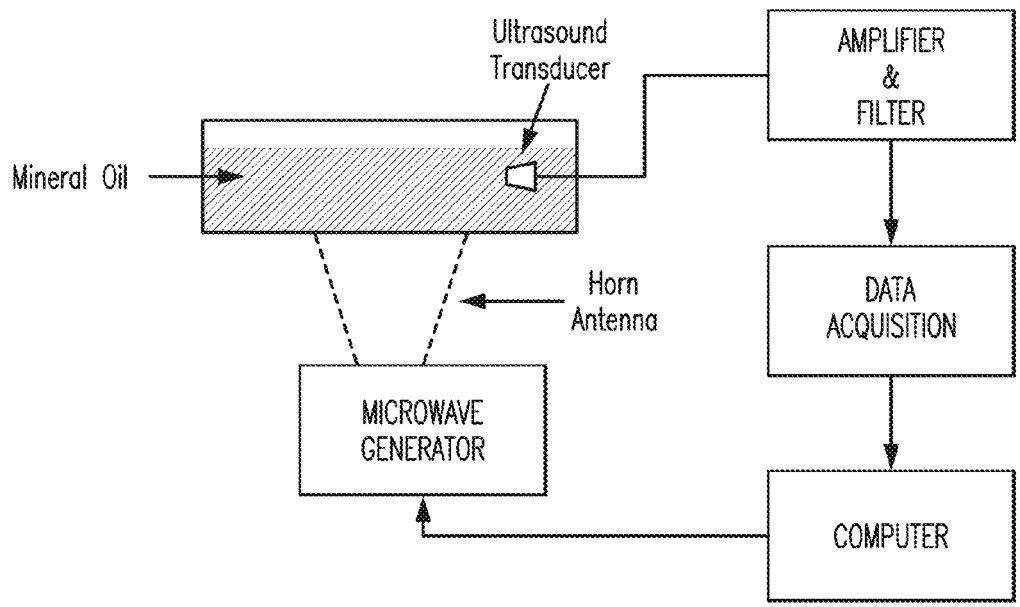
FIG. 3(A) shows the schematic depiction of the experimental setup for thermoacoustic signal measurements.

Thermoacoustic (TA) Imaging:

FIG. 3(A) is a schematic depiction of the experimental setup for TA measurements. The TA results were obtained from a TAT system. A 3.0-GHz microwave generator with pulse width of 0.6 µs and repetition rate of 10 Hz was employed as the excitation source. The pulses were guided toward the target through a horn antenna. The size of the antenna opening was 11 cm×7 cm. The average power density is 4.5 mW/cm$^2$ at the opening of the antenna, which is within the safety standard [36]. The test samples were placed in plastic tank filled with mineral oil for ultrasound coupling. A 1-MHz spherically focused transducer with a bandwidth of 70% (V314, Panametrics, Olympus) was used to receive TA signals. The received TA signals were amplified and stored by a data-acquisition (DAQ) card (CS 14200; Gage Applied, Lockport, Ill.) in a computer [37]. The microwave generator simultaneously triggered the data acquisition.

Results and Discussion:

In the past, bulk of the work performed towards developing CAs for PAT has been focused on metallic nanoparticles, organic dye molecules, and carbon nanotubes. In comparison to those CAs, graphene possesses several benefits: (1) Compared to carbon nanotubes, graphene possesses larger surface area, lower aspect ratio, and better dispersibility in most biological media. These properties are important, for most in vivo applications. Furthermore, colloidal dispersions (with high stability and less aggregation) of graphene sheets can be achieved without impurities that may be harmful in biological systems [38,39]. (2) The sp2 bonded carbon sheets of graphene can be directly functionalized for targeting and drug delivery [33]. For other PAT/TAT CAs, such as gold nanoparticles and organic dye molecules, to disperse and stabilize gold nanoparticles in solution or embed organic dye molecules, functionalization is performed on the biocompatible coating/capping agent. (3) O-GNPs and O-GNRs have been reported as CAs for other whole-body imaging applications such as magnetic resonance imaging [28] and nuclear imaging [32]. Therefore, they can be developed as multimodal CAs that provide complementary information at micro- to macro-scopic length scales. (4) Graphene can be developed as theragnostic (simultaneous therapy and diagnostics) agent combining PAT/TAT molecular imaging and NIR-induced hyperthermia [40]. Due to these unique features, graphene may serve as a platform for the design of multi-modal imaging and multi-therapeutic approaches.

The inventors compared the PA and TA signal amplitudes of oxidized single- and multi-walled graphene oxide nanoribbons (O-SWGNRs and O-MWGNRs), and oxidized graphene nanoplatelets (O-GNPs) to pristine single-walled carbon nanotubes (SWCNTs), pristine multi-walled carbon nanotubes (MWCNTs), pristine graphitic microparticles (GMPs), and oxidized graphitic microparticles (O-GMPs) to investigate the efficacy of graphene-like nanostructures and graphitic nano- or microstructure as potential contrast agents for PAT and TAT.

FIG. 1 shows representative transmission electron microscopy (TEM) images of all the nanomaterials used in the study (scanning electron microscopy (SEM) was used for GMPs). FIG. 1A displays that SWCNTs possessed nanotubes of lengths ~3-30 μm and nanotubes of widths ~1-2 nm and FIG. 1B displays that MWCNTs possessed nanotubes of lengths 0.5-200 μm and nanotubes of widths ~20-30 nm. FIG. 1C displays O-SWGNRs possessed nanoribbons of lengths ~0.5-1 μm and nanoribbons of widths ~3-6 nm and FIG. 1D displays O-MWGNRs possessed nanoribbons of lengths 0.5-1.5 μm and nanoribbons of widths ~60-90 nm. These confirm the complete unzipping of SWCNTs and MWCNTs ($\pi$*diameter). FIG. 1E displays that pristine GMPs were <45 μm in size. FIG. 1F displays that O-GMPs were loosely arranged sheets of a few layered graphene (~8 sheets, size >1 μm) whereas O-GNPs (FIG. 1G) had ~2-4 graphene sheets and diameters of ~5-15 nm.

Figure 2A:
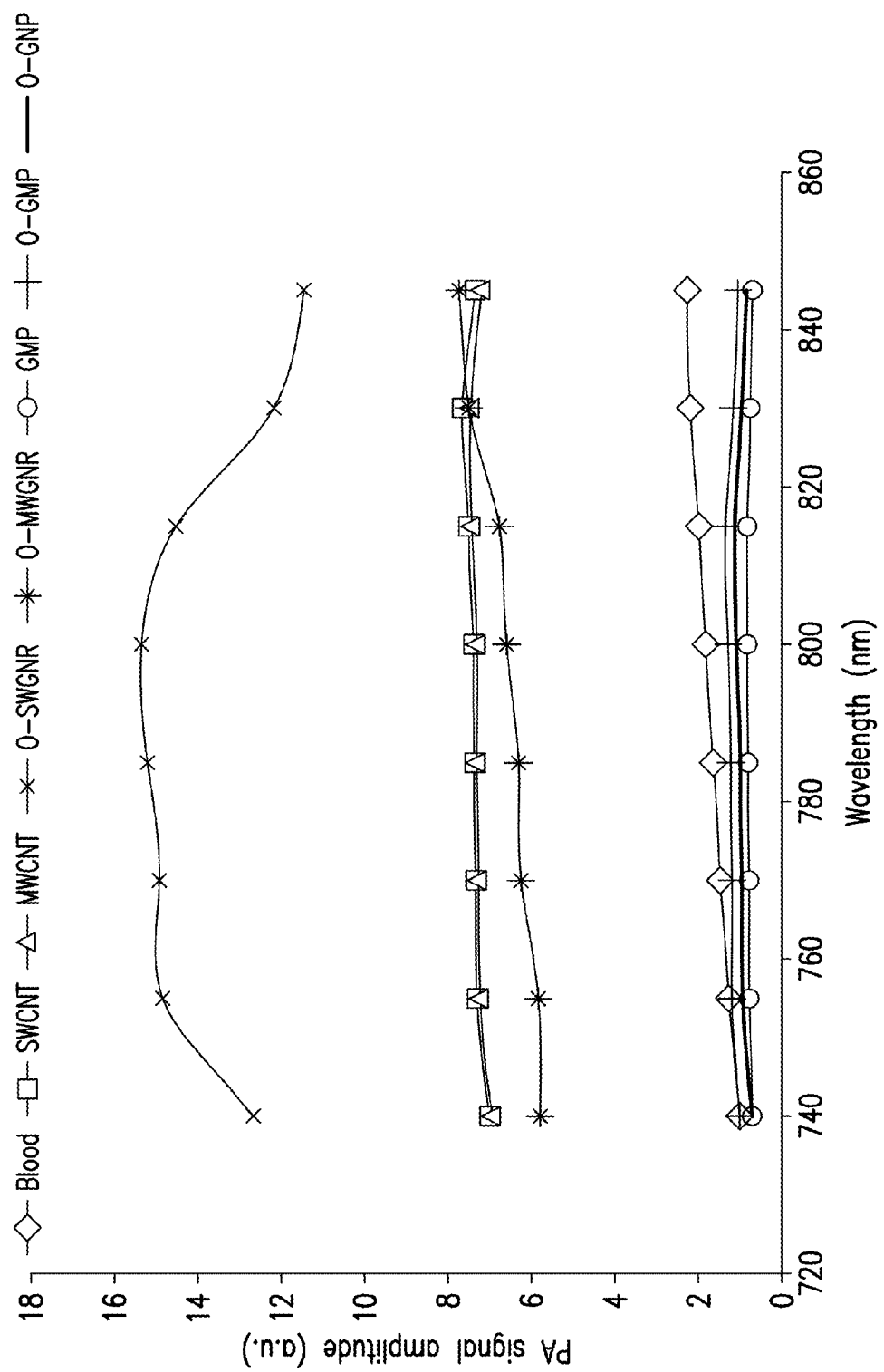
FIG. 2(A) shows photoacoustic spectral amplitudes of blood, single-walled carbon nanotubes (SWCNTs), multi-walled carbon nanotubes (MWCNTs), oxidized single-walled graphene nanoribbons (O-SWGNRs), oxidized multi-walled graphene nanoribbons (O-MWGNRs), micrographite flakes (GMPs), oxidized graphite microparticles (O-GMPs), and exfoliated graphene nanoplatelets (O-GNPs). PA signal amplitudes are normalized to that of blood at 740 nm.

Since hemoglobin is a dominant optical absorber which produces strong PA contrast in human tissue, the efficacy of graphene nanoparticles was first compared with blood in the near-infrared (NIR) wavelength window. FIG. 2(A) shows the PA signal amplitudes obtained from a tygon tube (I.D. 250 μm, O.D. 500 μm) filled with SWCNT, MWCNT, O-SWGNR, O-MWGNR, micro-graphite flakes, O-GMP, O-GNP and lysed bovine blood (905-250, Quad Five), respectively. The signals were normalized to that for blood at 740 nm. Table 1 below shows the PA spectrum (peak-to-peak PA signal amplitude versus excitation light wavelength) of these nanomaterials for an excitation wavelength range of 740-845 nm. The PA spectrum of blood is also shown in the same table.

As seen in Table 1B, at 755 nm excitation wavelength, the peak-to-peak PA signal amplitudes obtained from micro-graphite flakes, O-GMPs, and O-GNP were comparable to that from blood alone. In contrast, those from SWCNTs, MWCNTs, O-SWGNRs and O-MWGNRs (Table 1A) were more than 5 times stronger than that from blood, in which, O-SWGNRs showed ~12-14 times stronger signal.

TABLE 1 A

Photoacoustic signal amplitudes (a.u.) at 740-845 nm of graphene nanoribbons and control samples. PA signal amplitudes for all samples are normalized to that for blood at 740 nm.

| Wavelength (nm) | Blood | SWCNT | MWCNT | O-SWGNR | O-MWGNR |
|---|---|---|---|---|---|
| 740 | 1.00 | 7.02 | 7.00 | 12.65 | 5.78 |
| 755 | 1.26 | 7.31 | 7.23 | 14.85 | 5.84 |
| 770 | 1.47 | 7.34 | 7.27 | 14.92 | 6.25 |
| 785 | 1.65 | 7.39 | 7.30 | 15.22 | 6.33 |
| 800 | 1.84 | 7.41 | 7.32 | 15.33 | 6.60 |
| 815 | 2.00 | 7.51 | 7.44 | 14.52 | 6.79 |
| 830 | 2.21 | 7.64 | 7.45 | 12.21 | 7.50 |
| 845 | 2.31 | 7.35 | 7.20 | 11.45 | 7.73 |

TABLE 1 B

Photoacoustic signal amplitudes (a.u.) at 740-845 nm for graphene nanoplatelets and control samples. PA signal amplitudes for all samples are normalized to that for blood at 740 nm.

| Wavelength (nm) | Blood | GMP | O-GMP | O-GNP |
|---|---|---|---|---|
| 740 | 1.00 | 0.68 | 1.02 | 0.72 |
| 755 | 1.26 | 0.78 | 1.19 | 0.94 |
| 770 | 1.47 | 0.79 | 1.20 | 0.96 |
| 785 | 1.65 | 0.82 | 1.24 | 1.00 |
| 800 | 1.84 | 0.83 | 1.28 | 1.08 |
| 815 | 2.00 | 0.84 | 1.36 | 1.12 |
| 830 | 2.21 | 0.76 | 1.15 | 0.95 |
| 845 | 2.31 | 0.71 | 1.05 | 0.85 |

Figure 2B:
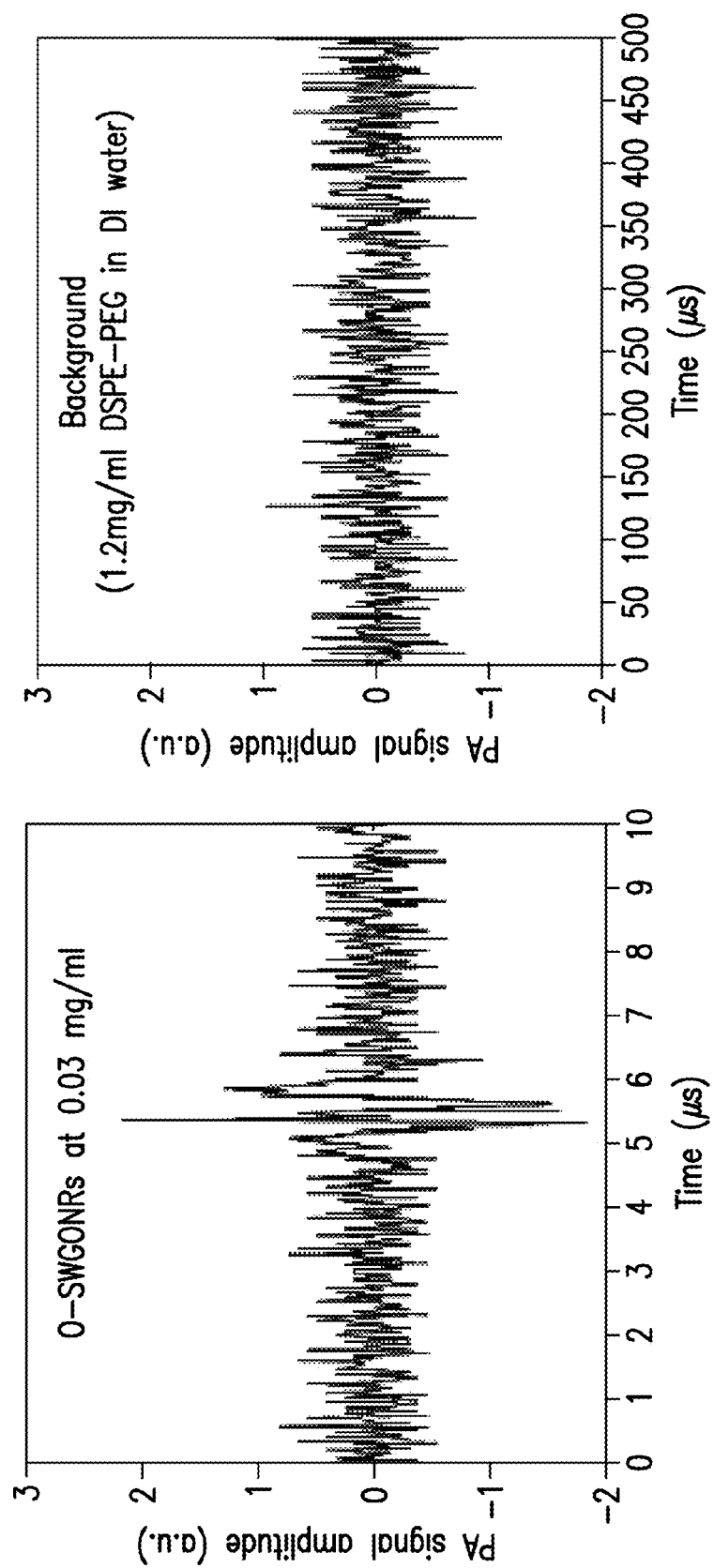
FIG. 2(B) shows PA signal amplitude of O-SWGNRs at 0.03 mg/ml concentration compared to background (1.2 mg/ml of DSPE-PEG solution).

The inventors also discovered that the concentration of the O-SWGNRs can be set as low as 0.03 mg/ml using PAT. At this low O-SWGNR concentration, a 2-fold increase in PA signal was measured compared to background (1.2 mg/ml of DSPE-PEG in DI water). FIG. 2(B) shows PA signal amplitude of O-SWGNRs at 0.03 mg/ml concentration. These results suggest that minimum detectable concentration of O-SWGNRs will be comparable to other PA contrast agents such as gold nanoparticles. Furthermore, the results showed that PA signal obtained from these nanomaterials exceeded inherent blood signal over the investigated NIR bandwidth, suggesting their utility for in vivo imaging.

Figure 3B:
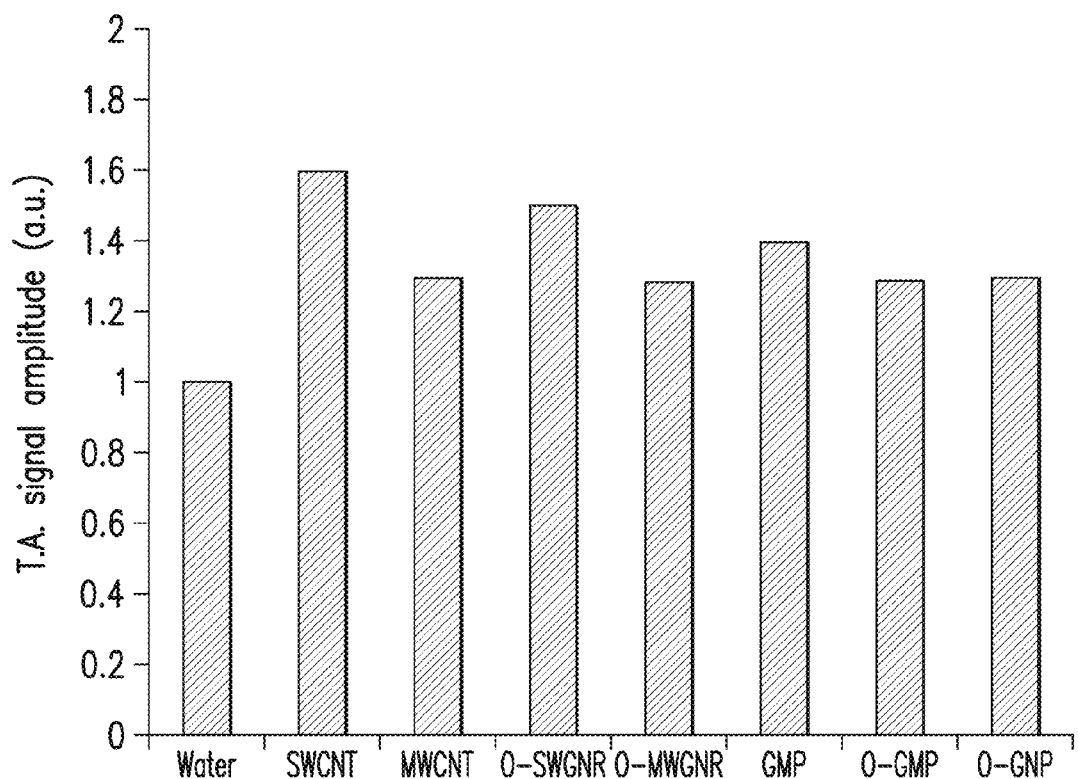
FIG. 3(B) shows thermoacoustic signal amplitudes of water, single-walled carbon nanotubes (SWCNTs), multi-walled carbon nanotubes (MWCNTs), oxidized single-walled graphene nanoribbons (O-SWGNRs), oxidized multi-walled graphene nanoribbons (O-MWGNRs), micrographite flakes (GMPs), oxidized graphite microparticles (O-GMP), and exfoliated graphene nanoplatelets (O-GNP) at 3 GHz. TA signals are normalized to that of water at 3 GHz.
Figure 3C:
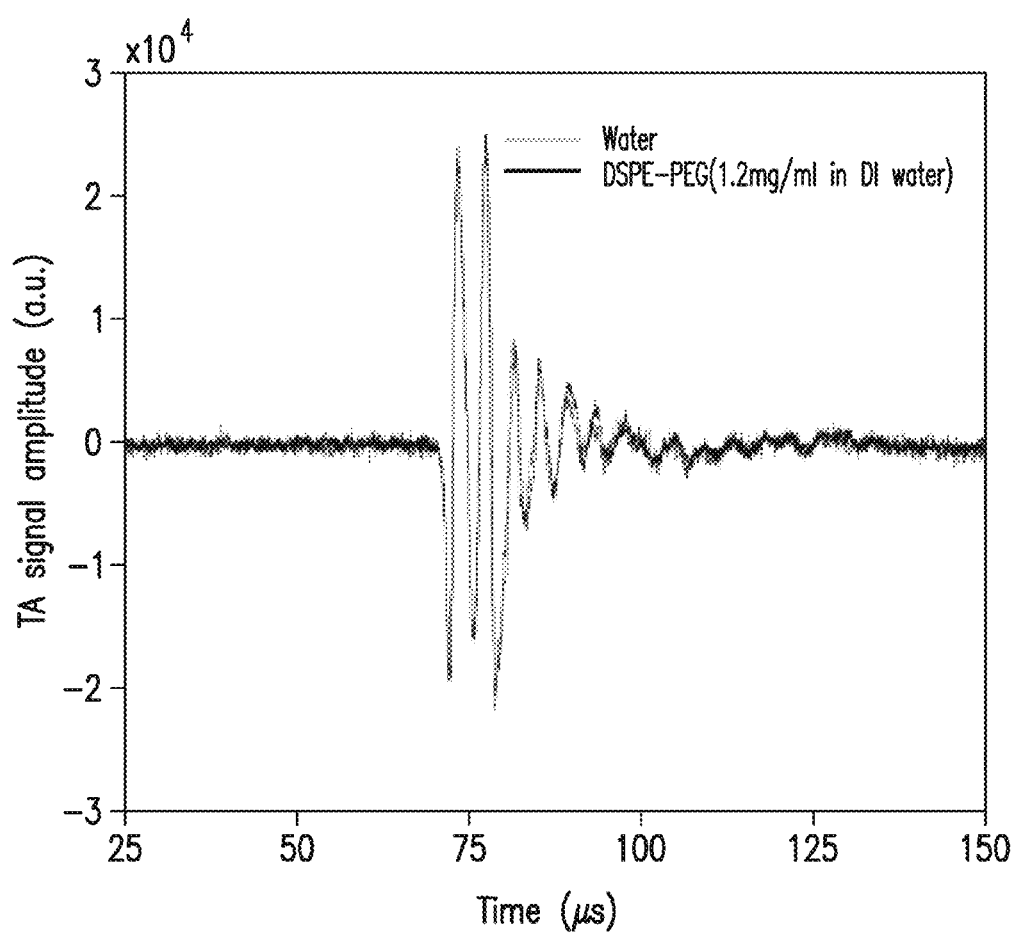
FIG. 3(C) shows TA signal amplitude of DSPE-PEG compared to deionized (DI) water.

For the TAT test, water and ions are two well-known sources of microwave absorbers in human tissue, and they generate strong TA signals. Therefore, to show that the graphene nanoparticles can function as contrast agents for TA, we compared the TA signal of the nanomaterials with that of deionized (DI) water. FIG. 3(B) shows the TA signals obtained from a low-density polyethylene (LDPE) vial (I.D.=6 mm and 1.5 cc volume) filled with DI water, SWCNTs, MWCNTs, O-SWGNRs, O-MWGNRs, GMPs, O-GMPs, and O-GNPs, respectively. The signal amplitudes were normalized to DI water. Additionally, TA signal amplitude of DSPE-PEG was comparable to DI water (see FIG. 3(C)), and the LDPE vial does not generate any measurable TA signal [21]. Table 2 below shows that at 3 GHz, O-SWGNRs, O-MWGNRs, O-GMP and O-GNPs exhibit approximately 10-28% TA signal enhancement compared to DI water.

TABLE 2

Thermoacoustic signal amplitudes (a.u.) at 3 GHz of graphene nanoribbons, graphene nanoplatelet and control samples. TA signal amplitudes have been normalized to that for water.

| Group | Signal Amplitude (a.u.) |
|---|---|
| Water | 1.00 |
| SWCNT | 1.59 |
| MWCNT | 1.29 |
| O-SWGNR | 1.5 |
| O-MWGNR | 1.28 |
| GMP | 1.39 |
| O-GMP | 1.28 |
| O-GNP | 1.29 |

In summary, these results demonstrated that among the nanomaterials, graphene nanoparticles O-SWGNRs and O-MWGNRs show promise as multi-modal PAT and TAT contrast agents, by exhibiting approximately 5-10 fold signal enhancement for photoacoustic tomography (PAT) in comparison to blood at the wavelength of 755 nm, and approximately 10-28% signal enhancement for thermoacoustic tomography (TAT) in comparison to water at 3 GHz, while O-GMP and O-GNPs show no significant signal enhancement for PAT, but approximately 12-29% signal enhancement for TAT. These results also suggesting that these nanomaterials may be utilized for in vivo imaging. All references cited herein are incorporated by reference in their entireties and for all purposes to the same extent as if each individual publication or patent or patent application was specifically and individually indicated to be incorporated by reference in its entirety for all purposes.

As will be apparent to those skilled in the art, many modifications and variations of the present invention can be made without departing from its spirit and scope.

The specific embodiments described herein are offered by way of example only, and the invention is to be limited only by the terms of the appended claims along with the full scope of equivalents to which such claims are entitled.

REFERENCES

1. Wang, L. V., *Nat Photonics* 2009, 3 (9), 503-509. DOI 10.1038/nphoton.2009.157.
2. Nie, L.; Ou, Z.; Yang, S.; Xing, D., *Med Phys* 2010, 37 (8), 4193-200.
3. Wang, X.; Pang, Y.; Ku, G.; Xie, X.; Stoica, G.; Wang, L. V., *Nat Biotechnol* 2003, 21 (7), 803-6. DOI 10.1038/nbt839 nbt839 [pii].
4. Hu, S.; Maslov, K.; Tsytsarev, V.; Wang, L. V., *J Biomed Opt* 2009, 14 (4), 040503. DOI 10.1117/1.3194136.
5. Pramanik, M.; Ku, G.; Li, C.; Wang, L. V., *Med Phys* 2008, 35 (6), 2218-23.
6. Ermilov, S. A.; Khamapirad, T.; Conjusteau, A.; Leonard, M. H.; Lacewell, R.; Mehta, K.; Miller, T.; Oraevsky, A. A., *J Biomed Opt* 2009, 14 (2), 024007. DOI 10.1117/1.3086616.
7. Zhang, H. F.; Maslov, K.; Stoica, G.; Wang, L. V., *Nat Biotechnol* 2006, 24 (7), 848-51. DOI nbt1220 [pii] 10.1038/nbt1220.
8. Weight, R. M.; Viator, J. A.; Dale, P. S.; Caldwell, C. W.; Lisle, A. E., *Opt Lett* 2006, 31 (20), 2998-3000. DOI 111347 [pii].
9. Siphanto, R. I.; Thumma, K. K.; Kolkman, R. G.; van Leeuwen, T. G.; de Mul, F. F.; van Neck, J. W.; van Adrichem, L. N.; Steenbergen, W., *Opt Express* 2005, 13 (1), 89-95. DOI 82287 [pii].
10. Li, M.; Oh, J.; Xie, X.; Ku, G.; Wang, W.; Li, C.; Lungu, G.; Stoica, G.; Wang, L. V., *PROCEEDINGS-IEEE* 2008, 96 (3), 481.
11. Kruger, R. A.; Kiser, W. L.; Reinecke, D. R.; Kruger, G. A.; Miller, K. D., *Mol Imaging* 2003, 2 (2), 113-23.
12. De la Zerda, A.; Zavaleta, C.; Keren, S.; Vaithilingam, S.; Bodapati, S.; Liu, Z.; Levi, J.; Smith, B. R.; Ma, T. J.; Oralkan, O.; Cheng, Z.; Chen, X.; Dai, H.; Khuri-Yakub, B. T.; Gambhir, S. S., *Nat Nanotechnol* 2008, 3 (9), 557-62. DOI nnano.2008.231 [pii] 10.1038/nnano.2008.231.
13. Cai, X.; Paratala, B. S.; Hu, S.; Sitharaman, B.; Wang, L. V., *Tissue Eng Part C Methods* 2012, 18 (4), 310-7. DOI 10.1089/ten.TEC.2011.0519.
14. Avti, P. K.; Hu, S.; Favazza, C.; Mikos, A. G.; Jansen, J. A.; Shroyer, K. R.; Wang, L. V.; Sitharaman, B., *PLoS One* 2012, 7 (4), e35064. DOI 10.1371/journal.pone.0035064.
15. Zhang, Y.; Cai, X.; Wang, Y.; Zhang, C.; Li, L.; Choi, S. W.; Wang, L. V.; Xia, Y., *Angewandte Chemie* 2011, 50 (32), 7359-63. DOI 10.1002/anie.201101659.
16. Mallidi, S.; Larson, T.; Aaron, J.; Sokolov, K.; Emelianov, S., *Opt Express* 2007, 15 (11), 6583-8. DOI 134710 [pii].
17. Agarwal, A.; Huang, S. W.; O'Donnell, M.; Day, K. C.; Day, M.; Kotov, N.; Ashkenazi, S., *Journal of Applied Physics* 2007, 102 (6), 064701-4.
18. Eghtedari, M.; Oraevsky, A.; Copland, J. A.; Kotov, N. A.; Conjusteau, A.; Motamedi, M., *Nano Lett* 2007, 7 (7), 1914-8. DOI 10.1021/nl070557d.
19. Wang, Y.; Xie, X.; Wang, X.; Ku, G.; Gill, K. L.; O'Neal, D. P.; Stoica, G.; Wang, L. V., *Nano Letters* 2004, 4 (9), 1689-1692. DOI 10.1021/nl049126a.
20. Pramanik, M.; Song, K. H.; Swierczewska, M.; Green, D.; Sitharaman, B.; Wang, L. V., *Physics in medicine and biology* 2009, 54 (11), 3291-301. DOI 10.1088/0031-9155/54/11/001.
21. Pramanik, M.; Swierczewska, M.; Green, D.; Sitharaman, B.; Wang, L. V., *J Biomed Opt* 2009, 14 (3), 034018. DOI 10.1117/1.3147407.
22. Wu, L.; Cai, X.; Nelson, K.; Xing, W.; Xia, J.; Zhang, R.; Stacy, A.; Luderer, M.; Lanza, G.; Wang, L.; Shen, B.; Pan, D., *Nano Res.* 2013, 1-14. DOI 10.1007/s12274-013-0308-8.
23. Yang, X.; Skrabalak, S. E.; Li, Z.-Y.; Xia, Y.; Wang, L. V., *Nano Letters* 2007, 7 (12), 3798-3802. DOI 10.1021/nl072349r.
24. Pan, D.; Cai, X.; Yalaz, C.; Senpan, A.; Omanakuttan, K.; Wickline, S. A.; Wang, L. V.; Lanza, G. M., *ACS nano* 2012, 6 (2), 1260-7. DOI 10.1021/nn203895n.
25. Cai, X.; Li, W.; Kim, C. H.; Yuan, Y.; Wang, L. V.; Xia, Y., *ACS nano* 2011, 5 (12), 9658-67. DOI 10.1021/nn203124x.
26. Kim, G.; Huang, S. W.; Day, K. C.; O'Donnell, M.; Agayan, R. R.; Day, M. A.; Kopelman, R.; Ashkenazi, S., *J Biomed Opt* 2007, 12 (4), 044020. DOI 10.1117/1.2771530.
27. Kosynkin, D. V.; Higginbotham, A. L.; Sinitskii, A.; Lomeda, J. R.; Dimiev, A.; Price, B. K.; Tour, J. M., *Nature* 2009, 458 (7240), 872-6. DOI 10.1038/nature07872.
28. Paratala, B. S.; Jacobson, B. D.; Kanakia, S.; Francis, L. D.; Sitharaman, B., *PLoS One* 2012, 7 (6), e38185. DOI 10.1371/journal.pone.0038185 PONE-D-12-06186 [pii].
29. Mullick Chowdhury, S.; Lalwani, G.; Zhang, K.; Yang, J. Y.; Neville, K.; Sitharaman, B., *Biomaterials* 2013, 34 (1), 283-293. DOI 10.1016/j.biomaterials.2012.09.057.
30. Lalwani, G.; Henslee, A. M.; Farshid, B.; Lin, L.; Kasper, F. K.; Qin, Y.-X.; Mikos, A. G.; Sitharaman, B., *Biomacromolecules* 2013, 14 (3), 900-909. DOI 10.1021/bm301995s.
31. Lalwani, G.; Kwaczala, A. T.; Kanakia, S.; Patel, S. C.; Judex, S.; Sitharaman, B., *Carbon* 2013, 53 (0), 90-100. DOI http://dx.doi.org/10.1016/j.carbon.2012.10.035.
32. Cornelissen, B.; Able, S.; Kersemans, V.; Waghorn, P. A.; Myhra, S.; Jurkshat, K.; Crossley, A.; Vallis, K. A., *Biomaterials* 2013, 34 (4), 1146-54. DOI 10.1016/j.biomaterials.2012.10.054.
33. Shen, H.; Zhang, L.; Liu, M.; Zhang, Z., *Theranostics* 2012, 2 (3), 283-94. DOI 10.7150/thno.3642.
34. Jastrzebska, A. M.; Kurtycz, P.; Olszyna, A. R., *Journal of nanoparticle research: an interdisciplinary forum for nanoscale science and technology* 2012, 14 (12), 1320. DOI 10.1007/s11051-012-1320-8.
35. Song, K. H.; Wang, L. V., *J Biomed Opt* 2007, 12 (6), 060503. DOI 10.1117/1.2818045.
36. (SCC39), I. I. C. o. E. S., *IEEE Std C95.1-2005 (Revision of IEEE Std C95.1-1991)* 2006, 1-238.
37. Nie, L.; Guo, Z.; Wang, L. V., *J Biomed Opt* 2011, 16 (7), 076005. DOI 10.1117/1.3595842.
38. Mao H Y, Laurent S, Chen W, Akhavan O, Imani M, Ashkarran A A, et al. Graphene: promises, facts, opportunities, and challenges in nanomedicine. *Chem Rev* 2013; 113: 3407-24.

39. Bussy C, Ali-Boucetta H, Kostarelos K. Safety considerations for graphene: lessons learnt from carbon nanotubes. *Accounts Chem Res* 2013; 46(3): 692-701.

40. Huang P, Xu C, Lin J, Wang C, Wang X, Zhang C, et al. Folic acid-conjugated graphene oxide loaded with photosensitizers for targeting photodynamic therapy. *Theranostics* 2011; 1: 2450.

What is claimed is:

1. A method of performing thermoacoustic imaging of a subject, comprising (a) administering to said subject a sufficient amount of a composition comprising (i) a magnetic composition comprising a magnetic metal or magnetic metal compound and a graphene nanostructure, wherein the metal or metal compound is intercalated in the graphene nanostructure; and (ii) one or more physiologically acceptable carriers or excipients; and (b) imaging said subject using a photoacoustic or thermoacoustic imaging device wherein said magnetic metal or metal compound is selected from the group consisting of Mn, Gd, and Fe.

2. The method of claim 1, wherein said graphene nanostructure has a thickness of 5 μm or less.

3. The method of claim 2, wherein said graphene nanostructure has a thickness of 1 to 5 μm.

4. The method of claim 1, wherein said graphene nanostructure has a thickness of about 20 nm or less.

5. The method of claim 4, wherein said graphene nanostructure comprises 2 to 12 atomic layers of carbon.

6. The method of claim 5, wherein said graphene nanostructure comprises 2 to 5 atomic layers of carbon.

7. The method of claim 5, wherein said graphene nanostructure comprises 2 to 4 atomic layers of carbon.

8. The method of claim 4, wherein said graphene nanostructure is a carbon nanoplatelet.

9. The method of claim 8, wherein said carbon nanoplatelet has an average diameter in the range of 5 to 100 nm.

10. The method of claim 9, wherein said carbon nanoplatelet has a diameter of about 5 to 50 nm.

11. The method of claim 9, wherein said carbon nanoplatelet has an average diameter of about 5-15 nm.

12. The method of claim 8, wherein said carbon nanoplatelet is an oxidized nanoplatelet.

13. The method of claim 4, wherein said graphene nanostructure is a carbon nanoribbon.

14. The method of claim 13, wherein said graphene nanostructure is a carbon nanoribbon having an average width in the range of 1 to 250 nm and an average length in the range of 200 to 5000 nm.

15. The method of claim 13, wherein said carbon nanoribbon has an average width of about 120 nm and an average length in the range of 600 to 2000 nm.

16. The method of claim 13, wherein said carbon nanoribbon is an oxidized nanoribbon.

17. The method of claim 1, further comprising a water solubilizing moiety attached to said graphene nanostructure.

18. The method of claim 17, wherein said water solubilizing moiety is covalently attached to said graphene nanostructure.

19. The composition of claim 17, wherein said water solubilizing moiety is selected from the group consisting of malonic acid, serinol malonodiamide, dextran, and cyclodextrins, attached to said graphene nanostructure.

20. The method of claim 1, wherein the composition is dispersed in a 1,2-distearoyl-sn-glycero-3-phosphoethanolamine-N-amino(polyethylene glycol) (DSPE-PEG) or Pluronic®.

21. The method of claim 1, wherein said subject is a mammal.

22. The method of claim 21, wherein said mammal is a human.

23. A method of performing photoacoustic imaging of a subject, comprising (a) administering to said subject a sufficient amount of a composition comprising (i) a magnetic composition comprising a magnetic metal or magnetic metal compound and a graphene nanostructure, wherein the metal or metal compound is intercalated in the graphene nanostructure, wherein the graphene nanostructure is a carbon nanoribbon; and (ii) one or more physiologically acceptable carriers or excipients; and (b) imaging said subject using a photoacoustic or thermoacoustic imaging device wherein said magnetic metal or metal compound is selected from the group consisting of Mn, Gd, and Fe.

24. The method of claim 23, wherein the carbon nanoribbon has a thickness of about 20 nm or less.

25. The method of claim 23, wherein the carbon nanoribbon has an average width in the range of 1 to 250 nm and an average length in the range of 200 to 5000 nm.

26. The method of claim 23, wherein the carbon nanoribbon has an average width of about 120 nm and an average length in the range of 600 to 2000 nm.

27. The method of claim 23, wherein said carbon nanoribbon is an oxidized nanoribbon.

28. The method of claim 23, wherein said subject is a mammal.

29. The method of claim 28, wherein said mammal is a human.

* * * * *